(12) United States Patent
Van Den Brink

(10) Patent No.: US 7,792,349 B2
(45) Date of Patent: Sep. 7, 2010

(54) METHOD AND DEVICE FOR INSPECTING A STRING OF DRUGS

(75) Inventor: Richard Rudolf Theodoor Van Den Brink, The Hague (NL)

(73) Assignee: Global Factories B.V., Es Den Haag (NL)

( * ) Notice: Subject to any disclaimer, the term of this patent is extended or adjusted under 35 U.S.C. 154(b) by 810 days.

(21) Appl. No.: 10/568,625

(22) PCT Filed: Aug. 19, 2004

(86) PCT No.: PCT/NL2004/000583
§ 371 (c)(1),
(2), (4) Date: Jun. 14, 2006

(87) PCT Pub. No.: WO2005/017814

PCT Pub. Date: Feb. 24, 2005

(65) Prior Publication Data
US 2007/0000805 A1    Jan. 4, 2007

(30) Foreign Application Priority Data
Aug. 19, 2003 (WO) ................. PCT/NL03/00592
Dec. 31, 2003 (NL) ................. 1025161

(51) Int. Cl.
*G06K 9/00* (2006.01)
(52) U.S. Cl. ................. 382/141; 382/140; 382/143; 382/142; 382/153
(58) Field of Classification Search ................. 382/141, 382/140, 143, 142, 153
See application file for complete search history.

(56) References Cited

U.S. PATENT DOCUMENTS

| 2,766,869 | A | | 10/1956 | Bauman |
| 5,543,972 | A | * | 8/1996 | Kamewada ................. 359/834 |
| 6,601,729 | B1 | | 8/2003 | Papp |
| 2002/0099467 | A1 | * | 7/2002 | Sleep et al. ................. 700/213 |
| 2002/0153056 | A1 | * | 10/2002 | Siegel et al. ................. 141/247 |
| 2003/0200726 | A1 | * | 10/2003 | Rast ................. 53/443 |

FOREIGN PATENT DOCUMENTS

WO    WO 02/25568 A2    3/2002

* cited by examiner

*Primary Examiner*—Matthew C Bella
*Assistant Examiner*—Mike Rahmjoo
(74) *Attorney, Agent, or Firm*—Sughrue Mion, PLLC

(57) ABSTRACT

Method and device for inspecting a string of packs. Each of the packs contains drugs, and consumer data such as patient data are provided on the packs. Specific characteristics of the drugs to be scanned are fed into a central processing unit. These characteristics are compared with the drugs present in the actual pack. According to the invention, a graphic image of the pack, the drugs and the patient data is produced and stored. To optimize scanning of a group of drugs spreading is proposed by means of a resilient cam which rotates in a plane essentially parallel with the plane of the carrier. Such cam is mounted in a bush and can move resiliently in said bush at right angles to the plane of the carrier and said bush is caused to rotate. It is possible to provide a number of such constructions adjacent to one another.

51 Claims, 6 Drawing Sheets

METHOD AND DEVICE FOR INSPECTING A STRING OF DRUGS

The present invention relates to a method for inspecting a group of drugs, comprising:
the infeed of patient and drug data;
conveying said drugs past a camera;
optical scanning said drugs by a camera;
comparing said scanned drugs with said infeed;
accepting or rejecting said drugs;
storing data relating to said drugs in a memory.

In WO 02/25568 A2 a method is disclosed, wherein a group of drugs is scanned under a camera. A processor/memory is provided to maintain patient database including a historical record of pill identification sessions and prescription information. Each pill identification session comprises scanning of the group of pills, analysing a pill image to extract pill identifying characteristics, including size, shape, colour, texture and markings, comparing the captured image with image stored in a database or library. U.S. Pat. No. 6,601,729 B1 relates to a drug inspection device having a camera, a camera monitor for displaying one after another the pictures taken by the camera and a graphic monitor for calling image data to be predescribed from a database and displaying thus called data. The picture of the drugs in each batch and the image data on the drugs corresponding to the drugs in each batch are displayed simultaneously on the respective monitors for the predetermined time and by visually checking the monitors a pharmacist can easily inspect drugs.

The drugs are packed in pack strings (for example Baxter strings).

Generally, such strings are put together in large pharmacies and the like. Such strings are each composed of, for example, seven compartments (client unit pack), in the case of which one or more drugs are present in a compartment for each day or part of a day. It is extremely important for the correct drugs to be placed in a pack, and checking systems for this are known. They consist of feeding the desired drugs to a central processing unit. With the aid of a camera and vision techniques, the numbers of drugs actually present in the pack are scanned and the specific data for them are fed to the central processing unit. Through comparison, it is determined whether these data correspond to each other and further handling of the string or pack is then authorized or otherwise.

In view of the great consequences of errors and the increasing level of claims for damage, increasingly high requirements are being set for the checking process. On the other hand, owing to increasing labour costs, every effort is being made to limit human involvement as much as possible. Finally, it is important at a later stage to be able to demonstrate if there are any errors what the status of the packs was at the time of inspection.

It is the object of the present invention to provide a method making it possible in a simple and efficient manner to ascertain at a later stage the extent to which the pack delivered was the correct one.

This aim is realised with a method such as described above in that several groups of drugs are inspected, wherein each group is provided in a pack and a number of packs is connected to provide a string, wherein each string is provided with patient data, said camera inspecting said packs and the group of drugs therein, wherein the scanned image of the patient data and packs having the groups of drugs therein, is entered in said memory.

According to the present invention, the pack is optically scanned by the camera, and the picture concerned is stored. In addition, the patient data are scanned by the same or a different camera and are likewise stored with the image of the pack. In this way proof of the state of the pack at the time of inspection is obtained, which proof is completely independent of and is separate from the data in the central memory. By storing these images in a memory, i.e. optical memory, the packer can prove at a later stage that his products left the packing station in a good state.

It will be understood that a group of drugs can comprise any number of drugs.

In contrast to WO 02/25568 A2 the image of both the patient data on the pack and the contents of the pack are registered. In WO 02/25568 A2 only the session is stored and not the image obtained from the session. According to the invention the ultimate proof for the presence or absence of certain drugs is obtained albeit at a somewhat higher requirement to the storage capacity of the memory.

It is possible to provide the patient consumer data on the end of a string or on each of the packs. In the last case each pack can have different data relating to the patient and the contents of the related pack. Generally, a pack corresponds to the quantity of drugs to be taken at one moment. For example, a patient can have three moments of taking drugs in a day, which means that three packs have to be opened in one day. A string can comprise a number of packs for one day or a number of packs for several days such as a week. The pack preferably consists of a transparent part and an opaque part. The opaque part serves as the background during the scan of the drugs, while the transparent part does not obstruct the scan. The patient data are preferably placed on the opaque part, so that they are easy to read out. In practice, this will be the "rear side" of the pack. According to a special embodiment of the present invention, scanning (generally in mirror image) of these data from the top through the transparent part and along the drugs and possibly subjecting them to a processing step mean that they can be stored so as to be readable in a standard manner, for example by way of a bitmap.

According to a preferred embodiment of the invention an input file is present at entering of the related pack/string into the device according to a sub subject invention.

At leaving of the pack/string the data of the input file, the scanned image and if available the data of counting of the number of articles such as tablets are entered in an output file. This output file contains all relevant data so that the input file can be removed from the memory. If a pack/string is rejected in the device the input file will not be deleted. This means that as long as there are input files in the system not all packs/strings have been processed and that further action of for example the operator is necessary.

The scanning of the drugs can comprise determining the number of drugs. However, according to an advantageous embodiment, the shape and/or colour of the drugs is/are (additionally) determined. For this purpose, a black and white camera that is suitable for determining the numbers of drugs is not sufficient, and a colour camera with appropriate special lighting must be used. Further optimising of the scanning and recognition process can be obtained if according to a preferred embodiment of the invention not only the number of drugs is counted but also the shape or other data thereof. This means that two characteristics of the groups of drugs are determined and brought together to check whether or not the required drugs are present in the packs. Such characteristics can include properties of the drugs. It is also possible to start with one characteristic and to continue with a further characteristic. For example, first of all, the shape of the individual pills can be determined after which a counting process of the number of drugs can take place. If the differences are too considerable this could mean that the device has to be further adjusted.

It might also be possible that one of the two characteristics determines whether or not a pack is rejected. In order to be able to scan the drugs accurately, it is proposed according to the present invention that by means of vibration and/or by means of brushes, the drugs as far as possible are prevented from lying on top of one another during the scanning process, in other words they lie clear of one another. Said spreading may be achieved by means of methods known in the prior art, for example with brushes. These are arranged in such a manner that their central axis of rotation runs essentially parallel with the carrier and by performing a brushing movement, the pills inside the pack are moved apart.

It has been found, however, that although such a method of spreading is satisfactory in many cases, there is no absolute guarantee that the pills are completely separated.

The present invention provides an improved method for spreading objects lying next to/on top of one another and objects that are standing on their side and need to be laid flat. The invention is not limited to separating objects inside a pack and lying on top of one another, such as the pills described above.

This object is achieved in the method described above in that said engagement comprises an annular movement in a plane essentially parallel to said carrier.

According to the present invention, the spreading operation is effected by an annular movement (optionally reciprocating) along a path in a plane parallel to the plane of the carrier. In contrast to the prior art, this will result in a more prolonged contact between the part of the spreading device which provides engagement with the object and the object itself. This more prolonged engagement enables complete separation under all circumstances. The continuous annular path described above is preferably a composite circular path, i.e. a path which consists of various circular movements.

According to an advantageous embodiment of the invention, the spreading occurs when the objects are being moved. This can be achieved very easily if the objects are disposed on a conveyor belt and are moved for any reason.

It must be understood that this method for spreading of drugs can also be used in combination with any other drug inspection device being different from the method as described in claim 1.

If the pack is accepted or rejected, this is preferably indicated by means of a mark such as a paint dot.

This checking can be based on colour and shape. Furthermore, the number of drugs concerned must be checked. Metal detection can also be carried out.

The present invention also relates to a device for inspecting a string of interconnected drug packs, comprising an infeed for a string of packs, conveyance means for said packs, a camera for scanning the drugs in said packs, a discharge for said string of packs, and also an input for patient/drug data, in addition to a comparison device for comparing said patient/drug data with said camera scans, scanning means being present for scanning of said patient data, and storage means being present for storing said patient scans and said drug scans. The conveyance means can comprise any construction known in the prior art, but according to an advantageous embodiment of the invention they consist of a belt. As indicated above, the data relating to the contents of the pack may come either from the outside or be incorporated in the pack itself, for example in the form of a barcode. Likewise, the patient data can either be scanned directly, or it may be present on the wall of the pack situated away from the camera. Patient data in that case would possibly appear in a mirror image on the storage medium. On the one hand, this need not be a problem because these data can be reversed again at the time of checking. On the other hand, it is easily possible by means of optical techniques to turn round the mirror image already at the time of storage of the patient data.

The relevant data are preferably taken as far as possible from the original order file. In other words, it is preferable not to make use of the data processed by the packer.

It is possible according to the present invention to operate the camera with different types of light. The light used for scanning the number and/or the shape of the drugs can be of a different wavelength from that of the light for making a "photograph" of the packs. This applies in particular if the shape and/or colour of the drugs has/have to be scanned. In that case special lighting is necessary. For simply determining the numbers and/or the name of the user lighting from the opposite side of the camera will suffice. When determining the shape and colour it is necessary to use further lighting from the position of the camera. If necessary the camera or the illumination means used for illuminating the packs can be provided with filters which could be adjustable.

The invention also relates to a device for spreading drugs lying next to/on top of one another, comprising a carrier for said drugs, as well as a spreading device disposed above said carrier and engaging on said objects, said spreading device comprising a cam-shaped part, which in the unloaded state is disposed directly above said carrier with clearance and is designed such that it is fastened to a drive in order to allow said cam-shaped part to follow a continuous path lying in a plane parallel to and above said carrier.

The circular movement described above can be achieved with driving motor.

According to a very advantageous embodiment of the invention, a double rotating movement is used. The cam-shaped parts or pins are arranged on arms or bushes, which arms or bushes can rotate about a first central axis. The cam-shaped parts are at a distance from said central axis and thus follow a circular movement. The bushes or arms are mounted on a support plate, which support plate can rotate about a second central axis. The first and second central axes are essentially parallel, but are at a distance from each other. This makes it possible to achieve a composite rotating movement.

Also for this device for spreading of drugs it should be understood that this can be used independently from the device described above i.e. can be combined with any drug inspection device.

The invention will be explained in greater detail below with reference to an exemplary embodiment shown in the drawings, in which.

Figure 4:
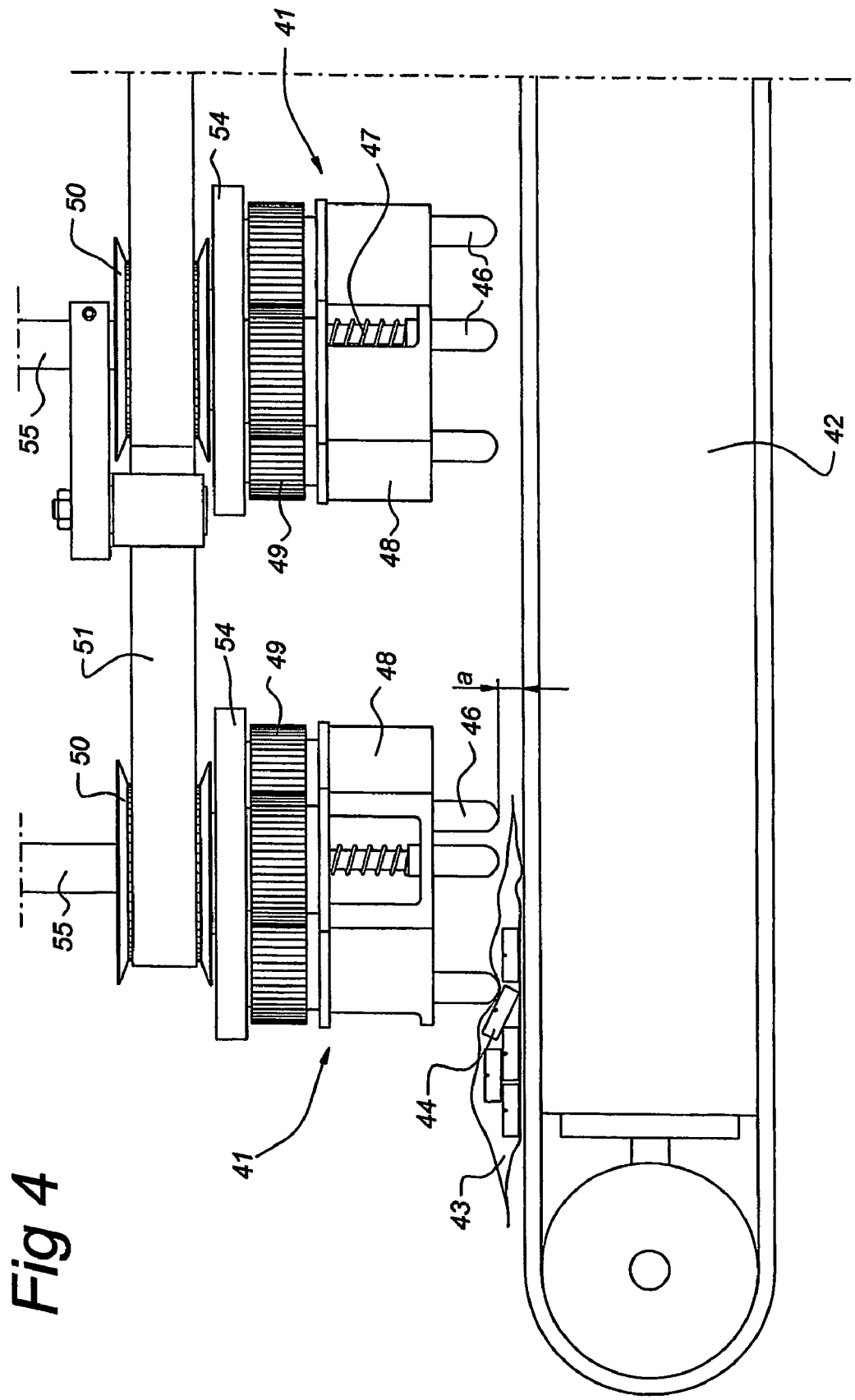
Figure 5:
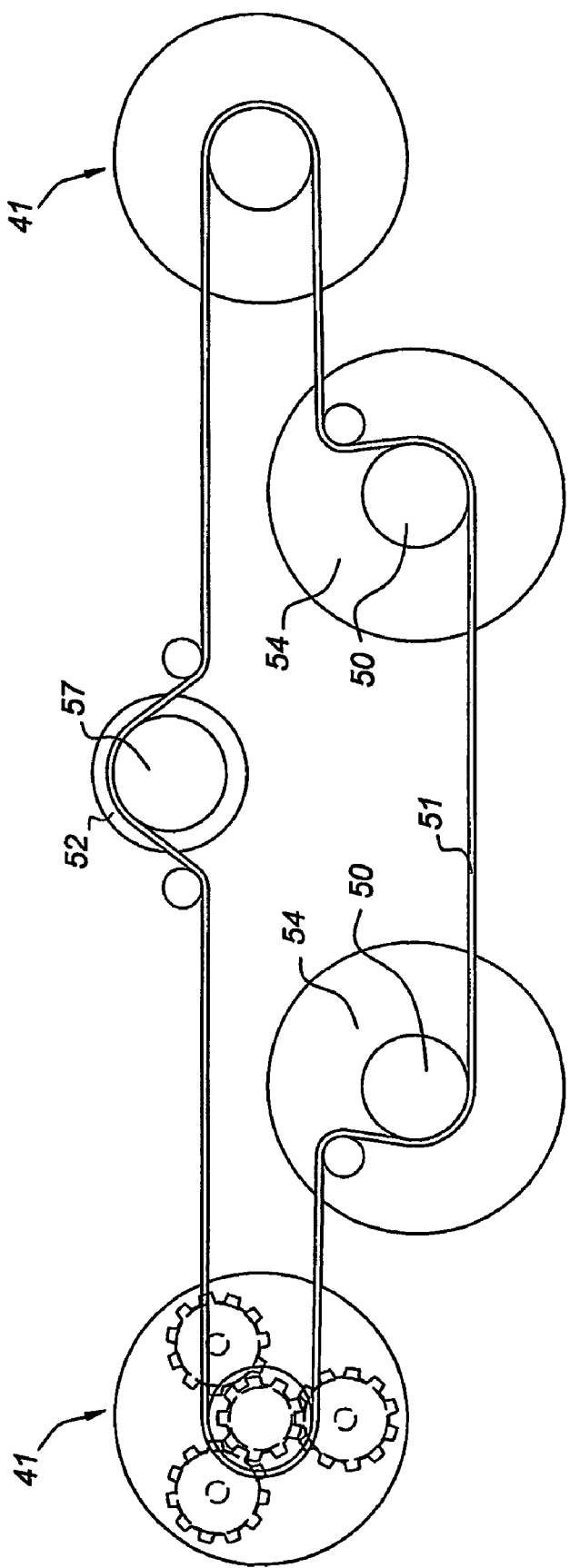
Figure 6:
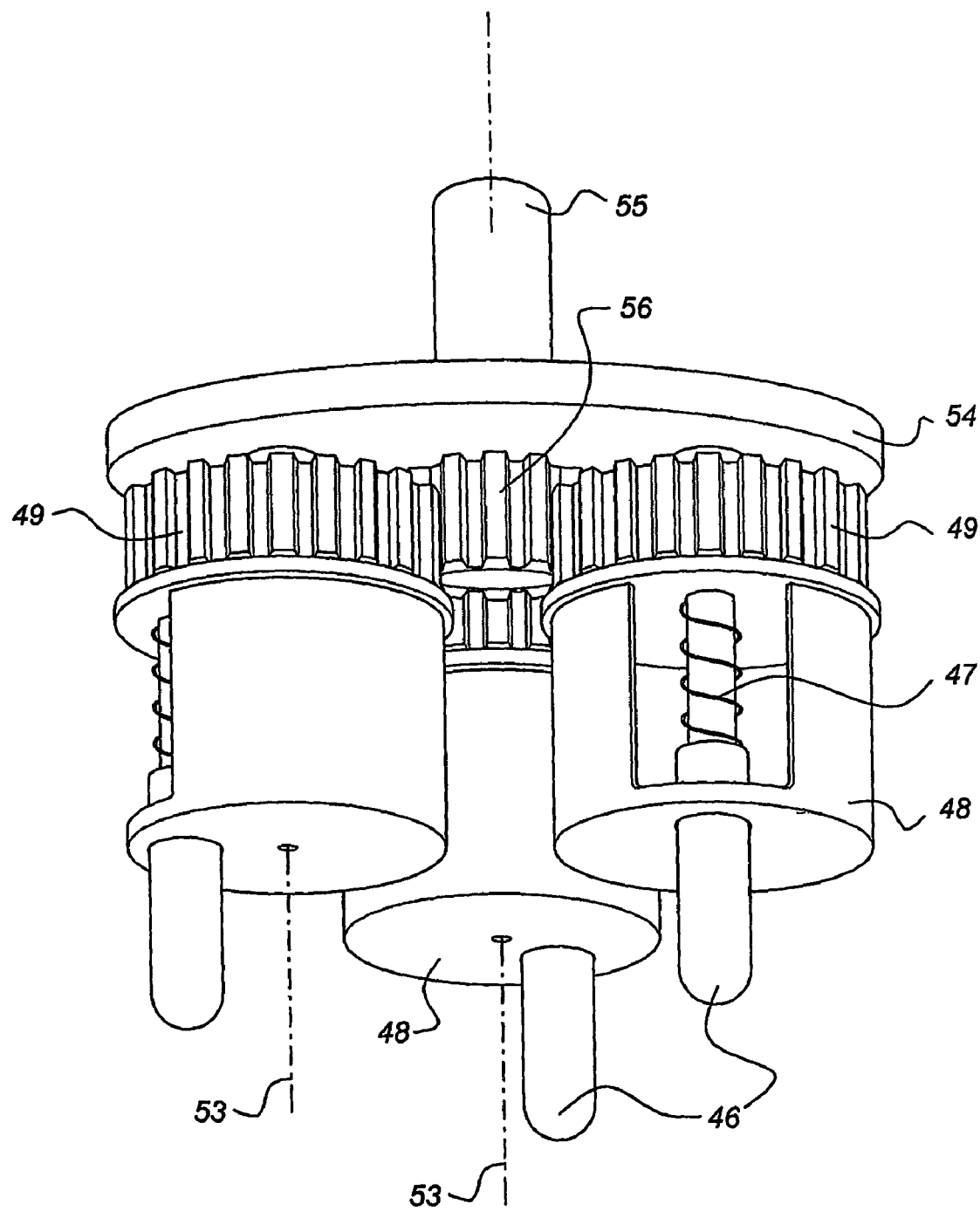

FIG. 4 diagrammatically shows a side view of the spreading means according to the invention;

FIG. 5 shows a plan view of the drive for the various spreading devices; and FIG. 6 shows a spreading device in detail.

Figure 1:
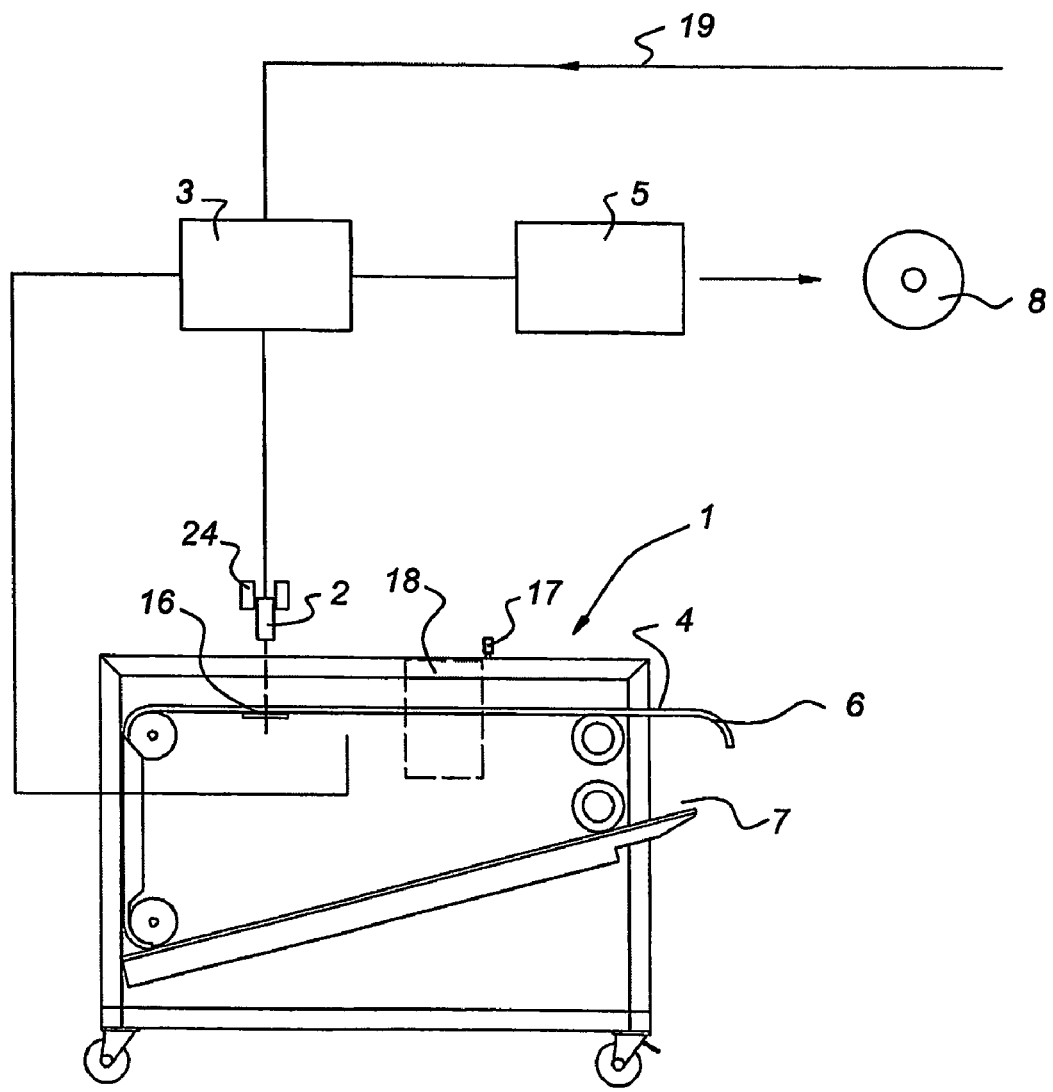
FIG. 1 shows very diagrammatically a device for inspecting drug packs.

In FIG. 1 reference numeral 1 indicates a device into which packs 10 of drugs can be introduced and subjected to an inspection operation. The infeed is indicated by 6 and the discharge by 7. The conveyance is achieved by means of a belt 4. After infeed 6 a brush 17 and also a vibrating plate 18 are present. Brush 17 or vibrating plate 18 could be omitted if desired. By these means the drugs, which are possibly lying on top of each other, are taken to a position lying beside each other. A camera 2 and a mirror 16 interacting with it are present. This camera is provided with one or two light sources.

A paint dot dispensing device 20 is present. It is capable of applying paint dots to the pack as they approach the discharge 7. Reference numeral 3 indicates a central processing unit, which is connected to the camera 2, to the paint dot dispensing device 20 and to a central input 19. This central processing unit 3 is connected to a DVD burner 5, by means of which DVDs 8 can be burnt.

Figure 2:
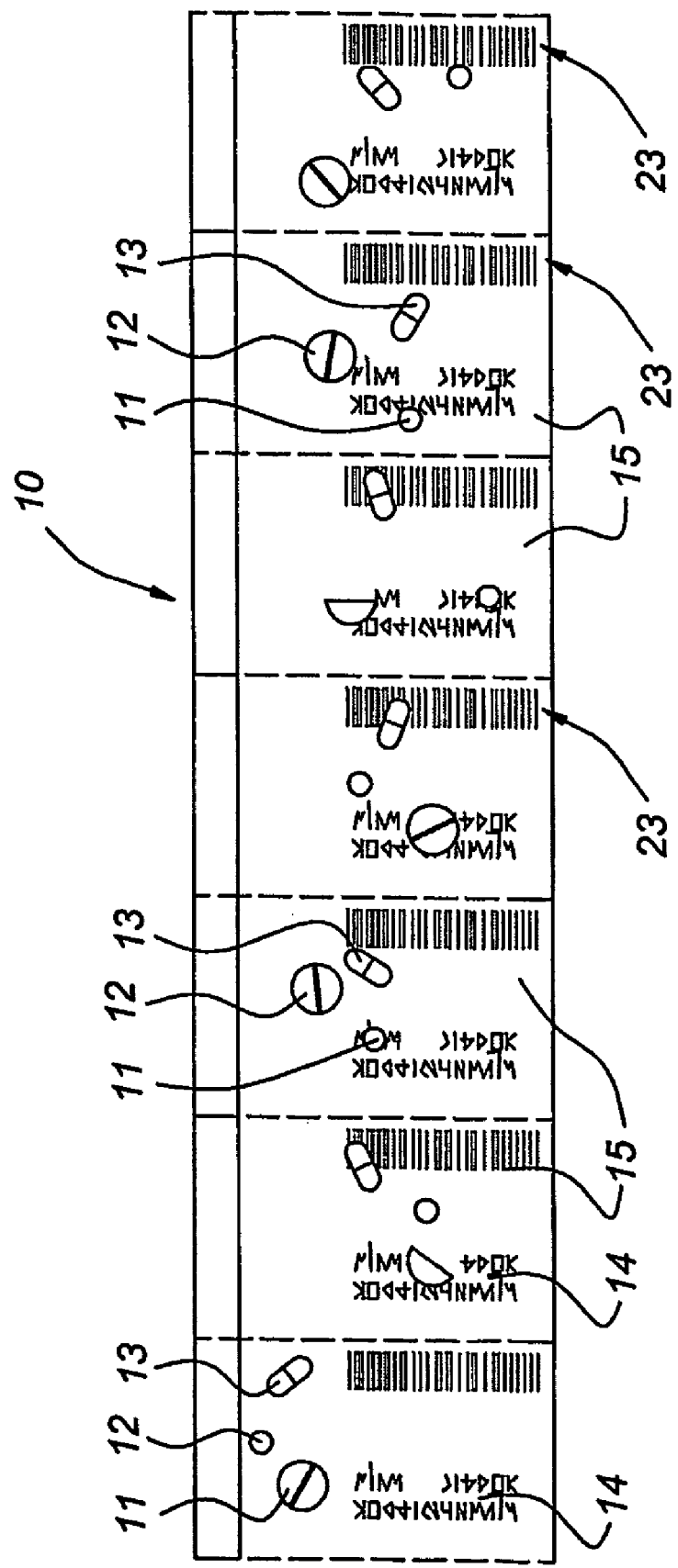
FIG. 2 shows an example of a drug pack.

FIG. 2 shows a drug pack. This drug pack is indicated in its entirety by 10 and consists of seven compartments 15 in which drugs 11-13 are placed. These drugs are in different shapes, colours and/or different numbers. This drug pack consists of two lengths of film placed one on top of the other. The top (in the drawing) length of film is of a transparent design, while the bottom one is of an opaque design, so that patient data 14 can be placed on the bottom length by means of a printer. Since such data are being placed on the outside, they will generally be placed on the underside. The barcode with patient data has reference numeral 23.

The device described above works as follows. After the introduction of a string 15 of packs into infeed 6, the belt 4 provides for conveyance of said string. If desired, gripping means (not shown in any further detail) may be present to grip (clamp) the string and provide for conveyance. Activation of the device can be achieved, for example, with the aid of an electronic eye, but it is also possible for the device to operate continuously. After movement along the brush 17 and vibrating plate 18, it can be assumed that the drugs have been placed in a position lying next to each other. The drugs are subsequently conveyed under camera 2. In the meantime, the data relating to the drugs that have to be placed in the pack have been fed in by way of input 19 into central processing unit 3. In this central processing unit or at an earlier stage the desired shape of the drugs and the number of drugs are determined from said data, in other words it is determined in the central processing unit what the readout of camera 2 ought to be. These limit target values are compared with the values delivered by the camera 2. Of course, it is likewise possible to determine the data for the drugs from the readout of camera 2 and subsequently to compare them with input 19. The pack is subsequently moved further and, depending on the result, a paint dot that determines acceptance or rejection is delivered by means of device 20.

According to the invention, a bottom light source 16 is present, by means of which light reaches the camera through the pack, so that the camera can also observe the underside of the pack. This makes it possible to scan the patient data by means of camera 2. The mirror image obtained in this way may be reversed electronically if desired.

According to the present invention, not only is the comparison described above made with the aid of a first light source, but it is also preferable by means of a second light source 24 (behind/beside the camera) to make a picture of both the top and bottom sides of the pack. This picture is stored on the DVD 8, which consequently provides proof of what is in the pack together with the data of the consumer. These data are entirely independent of the input at 19.

Should problems arise later, it is possible in a simple manner by means of the DVD 8 to ascertain how the pack left the packing station. All this can be made even easier by working with a tracking system.

Any other storage medium known in the prior art can be used instead of a DVD storage medium.

As a variant of the device described above, it is possible immediately after the infeed to determine the data of the string concerned by means of, for example, a barcode. By that means the data of the patient can be obtained.

Figure 3:
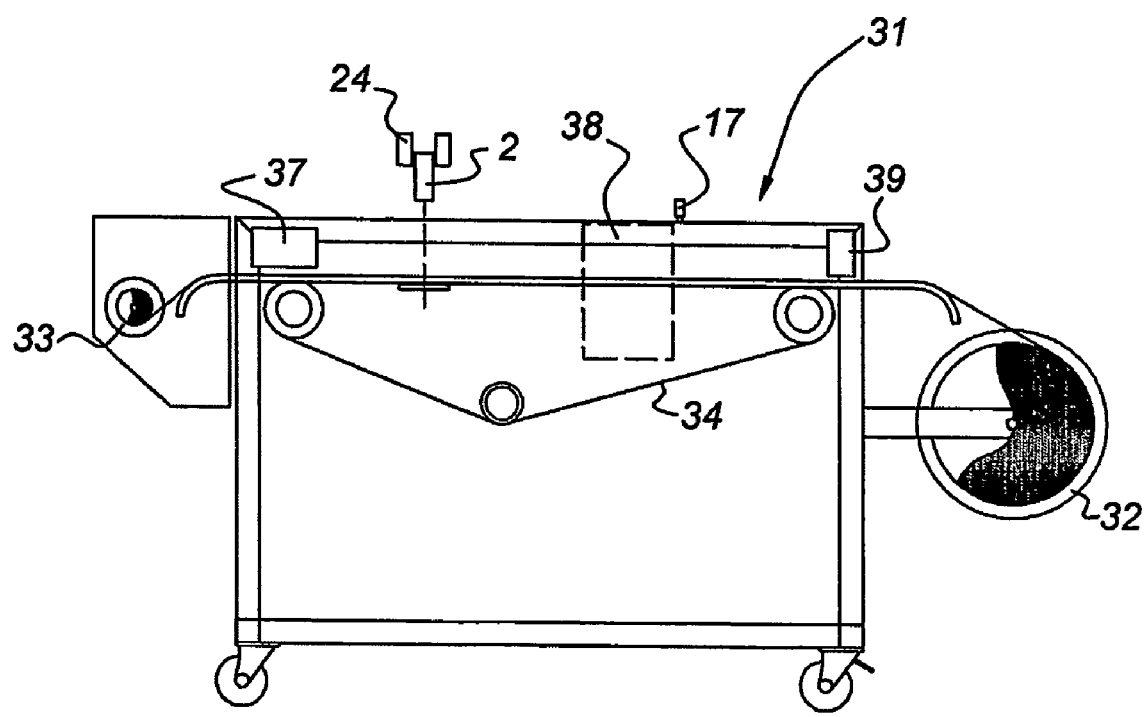
FIG. 3 shows a further device for inspecting drug packs.

A variant of the invention, indicated in its entirety by 31, is illustrated in FIG. 3. In the case of this embodiment the conveyance of the string of drug packs is realised in that the packs have originally been placed on a roll 32 and are wound off the latter and transferred to roll 33. A cutting station (not shown in any further detail) may, if desired, be present near the delivery end of the device, in order to cut the endless web into strings and possibly to remove them from a carrier. However, it is also possible to send the string coming off the roll 33 to a large-scale consumer (such as a hospital). The corresponding parts are indicated by the same reference numerals as those used in FIG. 1. Reference numeral 37 indicates a printer, while 38 indicates a metal detection unit. Reference numeral 39 indicates a barcode reader, which is capable of reading the data present on each of the packs. The conveyance can be assisted or even effected entirely by means of a belt 34.

With this device also, the patient data are collected with the aid of a camera, and more particularly with light coming from a source underneath. Likewise, the number of drugs is counted, and the colour and shape are determined. All this is optically stored by way of a bitmap.

FIG. 4 shows a number of spreading devices 41 which are arranged above a carrier 42, in this case a conveyor belt. By means thereof, packs 43, which contain pills 44, for example, can be displaced. As is evident from FIG. 4, some of these pills are on top of one another. For some procedures, such as inspections, it is necessary for the pills to be next to one another, for which purpose the spreading devices 41 according to the present invention are provided.

As is apparent from the figures, each spreading device consists of a cam-shaped part or pin 46. FIGS. 4 and 6 show that the latter is arranged to be resiliently displaceable by means of a spring 47 in an arm or bush 48. In the unloaded state, the pin 46 does not touch the carrier 42, but rather is at a very small distance a, for example 3-5 mm from the surface of the carrier. This distance is of course dependent on the product to be spread.

Each bush 48 is arranged on an auxiliary arm or plate 54 to be rotatable about a first central axis of rotation 53. As FIG. 6 shows, a number of bushes 48 are arranged rotatably on plate 54. Plate 54 is likewise rotatable about stationary shaft 55.

The bushes are each provided with toothing 49 at their top. The toothing 49 engages with a central toothed wheel 56 which is mounted fixedly on a stationary shaft 55. Driving motor 52 (FIG. 5) is provided with a transmission 51 which engages with a toothed wheel 50 that is connected to plate 54.

Rotation of the toothed wheel 50 will cause rotation of the plate 54 and thus of rotation shafts 53. Since the bushes 48 are coupled with the stationary toothed wheel 56 via toothed wheels 49, the bushes 48 will, in addition, perform a rotating movement about central axis 53.

In this manner, a specific area of the carrier is completely covered. By arranging a number of these spreading devices next to one another, the surface of a carrier can be completely covered in the transverse direction. In addition, arranging a number of spreading devices behind one another offers the advantage that complete spreading of the pills can always be ensured. Thus, when separating pills in drug packs, it is possible, for example, to install four of these spreading devices, each of which treats a part of a pack, an overlap being present in each case.

Variants will immediately spring to mind in the case of the person skilled in the art on reading the above description. For instance, it is possible to scan colours of the drugs or other data of the drugs. It is likewise possible to connect upstream a device for the detection of metal particles, in order to prevent metal particles from being present in the drugs. It is also possible to scan only a very limited part of the pack. These and further variants are obvious to the person skilled in the art and lie within the scope of the appended claims.

The invention claimed is:

1. A method for inspecting groups of drugs, comprising:
   providing the groups of drugs in packs and interconnecting the packs to provide strings;
   inputting patient and drug data;
   providing each string with at least some of the patient data;
   conveying said drugs;
   optical scanning said drugs in said packs and said patient data on said strings to read scanned patient and drug data and to produce an image of said packs and at least some of the patient data;
   entering into memory the scanned patient and drug data and the image of said packs and at least some of the patient data;
   comparing said scanned drug data with said input drug data;
   accepting or rejecting said drugs;
   wherein said stored image is maintained as proof of the state of the packs at the time of inspection.

2. The method according to claim 1, wherein said scanned drug data comprises the number of drugs.

3. The method according to claim 1, wherein said scanned drug data comprise the shape and/or colour of said drugs.

4. The method according to claim 1, wherein both the number of drugs and the shape thereof are used for comparing.

5. The method according to claim 1, wherein said acceptance/rejection comprises the application of a colour marking.

6. The method according to claim 1 wherein said scanned patient data are provided on each pack.

7. The method according to claim 1, wherein before the scanning of said drugs they are subjected to a treatment for spreading them out.

8. The method according to claim 7, wherein said treatment comprises applying vibration.

9. The method according to claim 7, wherein said treatment comprises moving a brush over said pack.

10. The method according to claim 7, further comprising the step of exerting a displacing engagement from above on said drugs, comprising an annular movement in a plane essentially parallel with a carrier on which the drugs are placed.

11. The method according to claim 10, wherein said step of exerting a displacing engagement comprises exerting resilient engagement in a direction at right angles to said carrier.

12. The method according to claim 10 wherein said annular movement comprises a circular movement.

13. The method according to claim 12, wherein the central axis of rotation is essentially at right angles to said carrier.

14. The method according to claim 13, wherein said objects are displaced during spreading in the plane of said carrier.

15. A device for inspecting a string of interconnected drug packs comprising:
   an infeed for a string of packs;
   conveyance means for said packs;
   a camera for scanning the drugs in said packs;
   a discharge for said string of packs;
   an input for patient/drug data;
   a comparison device for comparing said patient/drug data with said camera scans;
   scanning means for scanning of said patient data; and
   storage means for storing said patient data scans with said drug scans.

16. The device according to claim 15, wherein said conveyance means comprise a circulating belt with infeed and discharge provided near each other.

17. The device according to claim 15, wherein said scanning means comprise said camera scanning said patient data in a mirror image.

18. The device according to claim 15, wherein said camera comprises a first light source for determining the patient data and the number of drugs, and a second light source for determining the colour and/or shape of said drug scans.

19. The device according to claim 15, further comprising means for spreading drugs lying next to/on top of one another, comprising a carrier for said drugs, as well as a spreading device disposed above said carrier and engaging on said objects, said spreading device comprising a cam-shaped part, which in the unloaded state is disposed directly above said carrier with clearance and is designed in such a manner that it is fastened to a drive in order to allow said cam-shaped part to follow a continuous path lying in a plane parallel to and above said carrier.

20. The device according to claim 19, wherein said means for spreading comprise two spreading devices arranged next to one another.

21. The device according to claim 19, wherein said cam-shaped part is resiliently displaceable in a direction at right angles to said carrier.

22. The device according to claim 19, wherein said drive comprises a rotating motor provided with an arm which is at right angles to the direction of rotation and connected to the rotation shaft and on which said cam-shaped part is arranged.

23. The device according to claim 19, wherein said drive comprises a rotating motor, a transmission connected to the rotation shaft thereof and an auxiliary arm which is driven by said transmission and extends essentially at right angles to said carrier and is fitted with said arm on which the said cam parts are arranged.

24. The device according to claim 19, wherein said cam-shaped parts are arranged on an arm, said arm being rotatable about a first central axis of rotation, said arm being arranged on an auxiliary arm, said auxiliary arm being rotatable about a second central axis of rotation, said first and second central axes of rotation being at a distance from each other and running parallel to each other.

25. The device according to claim 24, wherein two arms with cam-shaped parts are arranged on said auxiliary arms.

26. Device according to claim 24, in which two arms with cam-shaped parts are arranged on said auxiliary arms.

27. The device according to claim 15, further comprising means for spreading out of said drugs disposed prior to said scanning means.

28. A method for inspecting groups of drugs, comprising;
   Providing the groups of the drugs in packs and interconnecting the packs to provide strings;
   the input of patient and drug data;
   conveying said drugs past a camera;
   optical scanning said drugs in said packs by a camera, said camera inspecting said packs, the group of drugs therein and the patient data provided on said strings;
   comparing said scanned drugs with said in-feed; and
   accepting or rejecting said drugs based on the inspection;
   wherein data relating to said drugs are stored in a memory, and the scanned image of the patient data and packs having the group of drugs therein, is entered in said memory for providing proof of the state of each pack at the time of inspection.

29. Method according to claim 28, in which said drug scan comprises the number of drugs.

30. Method according to claim 28, in which said drug scans comprise the shape and/or colour of said drugs.

31. Method according to claim 28, wherein both the number of drugs and the shape thereof are used for comparing.

32. Method according to claim 28, in which said acceptance/rejection comprises the application of a colour marking.

33. Method according to claim 28, in which said patient data are provided on each pack.

34. Method according to claim 28, in which before the scanning of said drugs they are subjected to a treatment for spreading them out.

35. Method according to claim 34, further comprising vibrating.

36. Method according to claim 34, further comprising moving with a brush over said pack.

37. Method according to one of claim 34, further comprising exerting a displacing engagement from above on said drugs, comprising an annular movement in a plane essentially parallel with a carrier on which the drugs are placed.

38. Method according to claim 37, said engagement comprising resilient engagement in a direction at right angles to said carrier.

39. Method according to claim 37, in which said annular movement comprises a circular movement.

40. Method according to claim 39, in which the central axis of rotation is essentially at right angles to said carrier.

41. Method according to claim 28, in which said objects are displaced during spreading in the plane of said carrier.

42. Device for inspecting a patient specific string of interconnected drug packs, comprising:
    an infeed for a string of packs, wherein patient data are provided on each pack;
    conveyance means for said packs;
    a camera for scanning the drugs in said packs and the patient data on said packs;
    a discharge for said string of packs; and
    an input for patient/drug data,
    wherein scanning means are present for scanning of said patient data, and also a comparison device for comparing said patient/drug data with said camera scans, and
    wherein storage means are provided for storing said patient data scans and said drug scans for providing proof of the state of each pack at the time of inspection.

43. Device according to claim 42, in which said conveyance means comprise a circulating belt with infeed and discharge provided near each other.

44. Device according to claim 42, in which said scanning means comprise said camera for scanning said patient data on said packs in a mirror image.

45. Device according to claim 42, in which said camera comprises a first light source for determining the patient data and the number of drugs, and a second light source for determining the colour and/or shape of said drug scans.

46. Device according to claim 42, further comprising means for spreading drugs lying next to/on top of one another, comprising a carrier for said drugs, as well as a spreading device disposed above said carrier and engaging on said objects, said spreading device comprising a cam-shaped part, which in the unloaded state is disposed directly above said carrier with clearance and is designed in such a manner that it is fastened to a drive in order to allow said cam-shaped part to follow a continuous path lying in a plane parallel to and above said carrier.

47. Device according to claim 46, in which said means comprise two spreading devices arranged next to one another.

48. Device according to claim 46, in which said cam-shaped part is resiliently displaceable in a direction at right angles to said carrier.

49. Device according to claim 46, in which said drive comprises a rotating motor provided with an arm which is at right angles to the direction of rotation and connected to the rotation shaft and on which said cam-shaped part is arranged.

50. Device according to claim 46, in which said drive comprises a rotating motor, a transmission connected to the rotation shaft thereof and an auxiliary arm which is driven by said transmission and extends essentially at right angles to said carrier and is fitted with said arm on which the said cam parts (46) are arranged.

51. Device according to claim 46, in which said cam-shaped parts (46) are arranged on an arm, said arm being rotatable about a first central axis of rotation, said arm being arranged on an auxiliary arm, said auxiliary arm being rotatable about a second central axis of rotation, said first and second central axes of rotation being at a distance from each other and running parallel to each other.

* * * * *